(12) United States Patent
Kwon et al.

(10) Patent No.: US 9,787,818 B2
(45) Date of Patent: Oct. 10, 2017

(54) EMERGENCY NOTIFICATION SYSTEM AND SERVER

(71) Applicant: Samsung Electronics Co., Ltd., Gyeonggi-do (KR)

(72) Inventors: Ki-Hyoun Kwon, Gyeonggi-do (KR); Em-Hwan Kim, Gyeonggi-do (KR); Jun-Ho Lee, Gyeonggi-do (KR); Jung-Su Kim, Gyeonggi-do (KR); Jang-Won Lee, Gyeonggi-do (KR); Jae-Hun Choe, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 1 day.

(21) Appl. No.: 14/808,644

(22) Filed: Jul. 24, 2015

(65) Prior Publication Data

US 2016/0080550 A1 Mar. 17, 2016

(30) Foreign Application Priority Data

Sep. 11, 2014 (KR) .................. 10-2014-0120294

(51) Int. Cl.
*H04M 11/04* (2006.01)
*H04M 1/725* (2006.01)
*H04W 4/22* (2009.01)
*H04W 4/02* (2009.01)

(52) U.S. Cl.
CPC ... *H04M 1/72538* (2013.01); *H04M 1/72572* (2013.01); *H04W 4/023* (2013.01); *H04W 4/22* (2013.01)

(58) Field of Classification Search
CPC ......... H04W 4/02; H04W 4/22; H04W 64/20; H04W 76/007

USPC ............... 455/404.1, 404.2, 556.1, 90.1
See application file for complete search history.

(56) References Cited

U.S. PATENT DOCUMENTS

| 8,107,920 | B2 | 1/2012 | Ben Ayed |
| 8,556,833 | B2 | 10/2013 | Otto |
| 2007/0173705 | A1 | 7/2007 | Teller et al. |
| 2011/0245633 | A1 | 10/2011 | Goldberg et al. |
| 2013/0178185 | A1 | 7/2013 | Park et al. |
| 2013/0317853 | A1 | 11/2013 | Tiburzi |
| 2013/0324072 | A1 | 12/2013 | Hsu |

(Continued)

FOREIGN PATENT DOCUMENTS

| JP | 2004-129905 | 4/2004 |
| JP | 2006-141902 | 6/2006 |

(Continued)

*Primary Examiner* — Temica M Beamer
(74) *Attorney, Agent, or Firm* — The Farrell Law Firm, P.C.

(57) ABSTRACT

An emergency notification system and server are provided. The emergency notification system includes a wearable device that senses biosignals of a user wearing the wearable device and captures environment data; and a mobile device that periodically receives at least one of the biosignals and the environment data from the wearable device, determines a distance between the mobile device and the wearable device, periodically transmits the at least one of the biosignals and the environment data to a server, requests the wearable device to provide the at least one of the biosignals and the environment data, and transmits the received at least one of the biosignals and the environment data to the server.

18 Claims, 13 Drawing Sheets

(56) References Cited

U.S. PATENT DOCUMENTS

| | | | |
|---|---|---|---|
| 2014/0306799 A1* | 10/2014 | Ricci | B60Q 1/00 340/5.83 |
| 2014/0306826 A1* | 10/2014 | Ricci | H04W 48/04 340/573.1 |
| 2015/0137983 A1* | 5/2015 | Johnson, Jr. | G06K 7/0095 340/632 |
| 2016/0035204 A1* | 2/2016 | Jansen | H04W 4/02 340/573.1 |

FOREIGN PATENT DOCUMENTS

| KR | 10-2012-0085065 | 7/2012 |
|---|---|---|
| KR | 10-2013-0096085 | 8/2013 |

* cited by examiner

EMERGENCY NOTIFICATION SYSTEM AND SERVER

This application claims priority under 35 U.S.C. §119(a) to Korean Patent Application No. 10-2014-0120294, which was filed in the Korean Intellectual Property Office on Sep. 11, 2014, the entire disclosure of which is incorporated herein by reference.

BACKGROUND

1. Field of the Invention

The present disclosure relates generally to an emergency notification system and server.

2. Description of the Related Art

With the exponential development of the healthcare industry and the advancement of communication facilities, a Ubiquitous Healthcare (U-Health) system is currently being established. The U-Health system continuously transmits biometric information collected, for example, through a portable device, to a U-Health server or a medical institution, allowing doctors to remotely observe biometric information of a patient.

In the U-Health system, when an emergency situation occurs, it is important to quickly identify the location of a patient. More specifically, the location and state information of an emergency patient should be quickly transmitted to an emergency rescue system or a mobile terminal of the emergency rescue system.

In the U-Health system, wearable devices that are specialized for healthcare may be provided. These wearable devices sense and analyze a user's health information, and call to a relevant agency in the event of an emergency situation.

SUMMARY

The present disclosure is made to address at least the problems described above and to provide at least the advantages described below.

An aspect of the present disclosure is to provide an emergency notification system that identifies an emergency situation occurrence and, in response, provides biometric information, global positioning system (GPS) information, and data, such as a sound or an image, to another party, e.g., a guardian or a relevant emergency agency.

Another aspect of the present disclosure is to provide an emergency notification server that identifies an emergency situation occurrence and, in response, provides biometric information, GPS information, and data to another party.

In accordance with an aspect of the present disclosure, an emergency notification system is provided, which includes a wearable device that senses biosignals of a user wearing the wearable device and captures environment data; and a mobile device, which is wirelessly connected to the wearable device, that periodically receives at least one of the biosignals and the environment data from the wearable device, determines a distance between the mobile device and the wearable device, based on an intensity of an adjacent signal received from the wearable device, periodically transmits the at least one of the biosignals and the environment data to a server, requests the wearable device to provide the at least one of the biosignals and the environment data, and transmits the received at least one of the biosignals and the environment data to the server, when the intensity of the adjacent signal is less than or equal to a preset value or when an emergency signal is received from the server.

In accordance with another aspect of the present disclosure, an emergency notification server is provided, which includes a transceiver that periodically receives, from a first mobile device, biosignals and an intensity of an adjacent signal between the first mobile device and a wearable device that senses the biosignals; and a controller that determines whether an emergency situation has occurred, based on the received biosignals, generates an emergency signal requesting the first mobile device to provide data comprising a most recently received sound and image, when the intensity of the adjacent signal is less than or equal to a preset value or when the emergency situation has occurred, and controls the transceiver to transmit the emergency signal to the first mobile device or to transmit the emergency signal and the data to a second mobile device.

In accordance with another aspect of the present disclosure, a mobile device is provided, which is wirelessly connected to a wearable device. The mobile device includes a transceiver that periodically receives, from the wearable device, at least one of biosignals sensed by the wearable device and environment data captured by the wearable device, and that periodically transmits the received at least one of the biosignals and the environment data to a server; and a controller that requests the wearable device to provide the at least one of the biosignals and the environment data, determines whether an emergency situation has occurred, based on the received at least one of the biosignals and the environment data, and controls the transceiver to transmit an emergency signal to the wearable device, when the emergency situation has occurred.

BRIEF DESCRIPTION OF THE DRAWINGS

The above and other aspects, features, and advantages of the present disclosure will become more apparent from the following detailed description taken in conjunction with the accompanying drawings, in which.

DETAILED DESCRIPTION OF THE EMBODIMENTS

Figure 1:
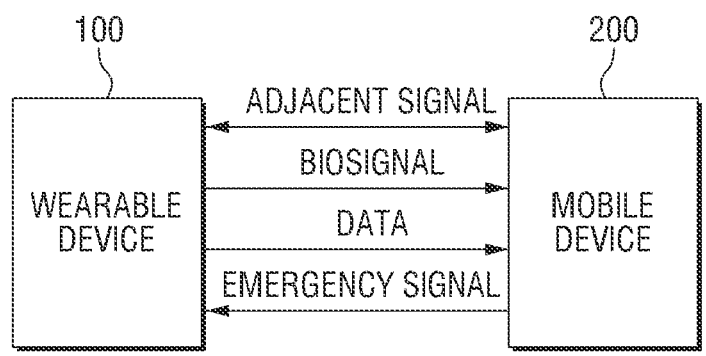
FIG. 1 illustrates an emergency notification system according to an embodiment of the present disclosure.

Various embodiments of the present disclosure will now be described in detail with reference to the accompanying drawings. In the following description, specific details such as detailed configuration and components are merely provided to assist the overall understanding of these embodiments of the present disclosure. Therefore, it should be apparent to those skilled in the art that various changes and modifications of the embodiments described herein can be made without departing from the scope and spirit of the present disclosure. In addition, descriptions of well-known functions and constructions are omitted for clarity and conciseness.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this disclosure, specify the presence of stated features, integers, steps, operations, elements, and/or components, but do not preclude the presence or addition of one or more other features, integers, steps, operations, elements, components, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below may be referred to as a second element, component, region, layer or section without departing from the teachings of the present disclosure.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

Embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present inventive concept.

Unless otherwise defined, all terms (including technical and scientific terms) used herein have the same meaning as commonly understood by one of ordinary skill in the art to which the present disclosure belongs. It will be further understood that terms, such as those defined in commonly used dictionaries, should be interpreted as having a meaning that is consistent with their meaning in the context of the relevant art and this specification, and should not be interpreted in an idealized or overly formal sense unless expressly so defined herein.

FIG. 1 illustrates an emergency notification system according to an embodiment of the present disclosure.

Referring to FIG. 1, the emergency notification system includes a wearable device 100 and a mobile device 200.

The wearable device 100 is worn on or attached to the body to sense biosignals and to capture data including an external sound and/or an image. For example, the wearable device 100 may be made of a flexible material and worn by a user in various forms including, but not limited to, clothes, shoes, gloves, glasses, hats, and accessories that can be worn on the body of a person or animal.

The wearable device 100 may be paired with the mobile device 200 using wireless communication. For example, the wearable device 100 communicates with the mobile device 200 through radio frequency (RF) communication and may include various types of sensors. In addition, the wearable device 100 may use a local area network such as a wireless personal area network (WPAN) or Zigbee.

The mobile device 200 wirelessly connects to the wearable device 100. Examples of the mobile device 200 include a general mobile communication terminal, a terminal capable of providing WiBro wireless network service, a personal data assistant (PDA), and a smartphone.

The mobile device 200 may be equipped with an interface (such as an IEEE 802.11 wireless local area network (WLAN) card) for WLAN connection.

The mobile device 200 may also be an information communication device (such as a computer, a notebook computer, etc.) equipped with a WLAN connection interface or an apparatus including the information communication device. The mobile device 200 may include a display module having a touch screen that serves as an input interface.

As illustrated in FIG. 1, the wearable device 100 and the mobile device 200 exchange adjacent signals. An adjacent signal is used to measure a distance between the wearable device 100 and the mobile device 200. For example, the adjacent signal may use a local area wireless communication method such as an RF signal, an infrared signal, an ultrasonic signal, Bluetooth®, or near-field communication (NFC).

The wearable device 100 may periodically transmit a user's biosignals to the mobile device 200. In addition, the wearable device 100 may record an external sound and/or capture an image of a current situation using an external input device and transmit the recorded sound and/or captured image to the mobile device 200. The wearable device 100 may periodically transmit data including a sound and/or an image to the mobile device 200. However, the wearable device 100 may also transmit data including a sound or an image, in response to a request from the mobile device 200.

The mobile device 200 may transmit an emergency signal to the wearable device 100. When receiving the emergency signal, the wearable device 100 may record an external sound and/or capture an image, and transmit the sound and/or the image to the mobile device 200.

Figure 2:
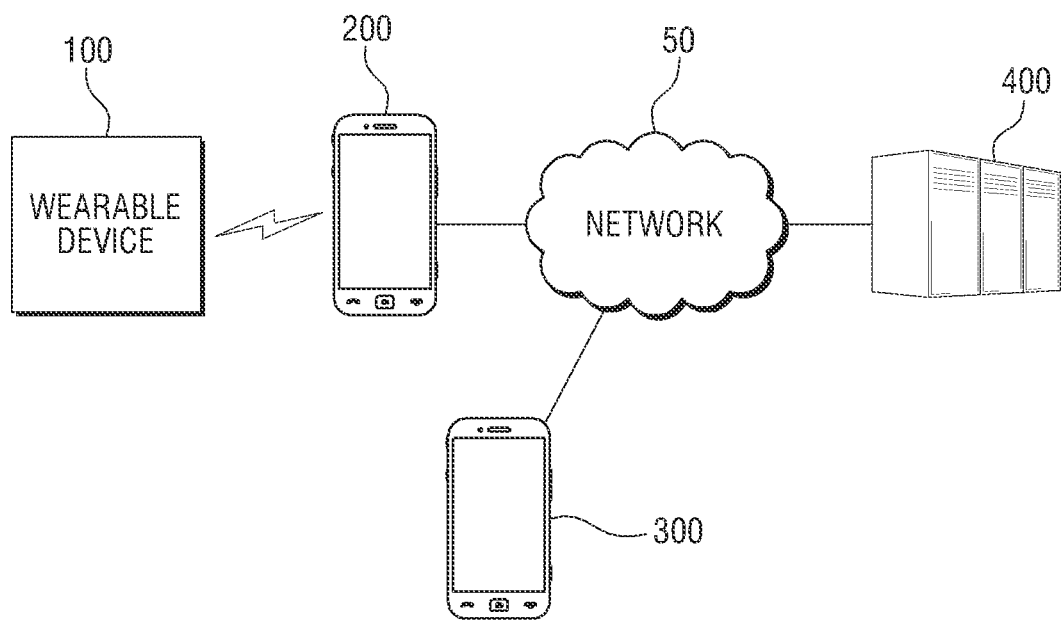
FIG. 2 illustrates an emergency notification system according to an embodiment of the present disclosure.

FIG. 2 illustrates an emergency notification system according to an embodiment of the present disclosure.

Referring to FIG. 2, the emergency notification system includes a wearable device 100, a mobile device 200, a second mobile device 300, and a server 400. The wearable device 100 and the mobile device 200 have already been described above with reference to FIG. 1, and therefore, will not be described again in detail with reference to FIG. 2.

The wearable device 100, the mobile device 200, and the second mobile device 300 communicate through a network 50. Examples of the network 50 include 3G, 4G, WiFi, and Internet networks.

Additionally, a communication network between the wearable device 100 and the mobile device 200 may be different from a communication network between the mobile device 200 and the server 400. For example, the wearable device 100 and the mobile device 200 may be connected to each other through WiFi, while the mobile device 200 and the server 400 may be connected to each other through the Internet.

The second mobile device 300 may be an electronic device (such as a smartphone or a tablet PC) of a guardian of a user wearing the wearable device 100 or a relevant emergency agency.

Contact information of the guardian may be registered in advance with the mobile device 200. The guardian may be a number of people, and the people may be included in a receiver group and managed accordingly. The receiver group can be modified using the mobile device 200 or the second mobile device 300.

The relevant emergency agency may be an agency that checks a health condition of the user wearing the wearable device 100 or that identifies an emergency situation occurrence.

The server 400 may receive measured biosignals, GPS information, and data including an image or a sound from the wearable device 100. The server 400 may determine whether an emergency situation has occurred using the received biosignals.

In addition, the server 400 may receive the intensity of an adjacent signal from the mobile device 200. If the intensity of the adjacent signal is less than or equal to a preset value, the server 400 may determine that an emergency situation has occurred.

When identifying an emergency situation occurrence, the server 400 may transmit an emergency signal to the mobile device 200. Thereafter, the mobile device 200 may transmit the emergency signal to the wearable device 100 in order to request GPS information of the user and data including an image or a sound of the current situation. In response to the request from the mobile device 200, the wearable device 100 may transmit the data to the mobile device 200. Thereafter, the mobile device 200 may transmit the received data to the server 400.

Figure 3:
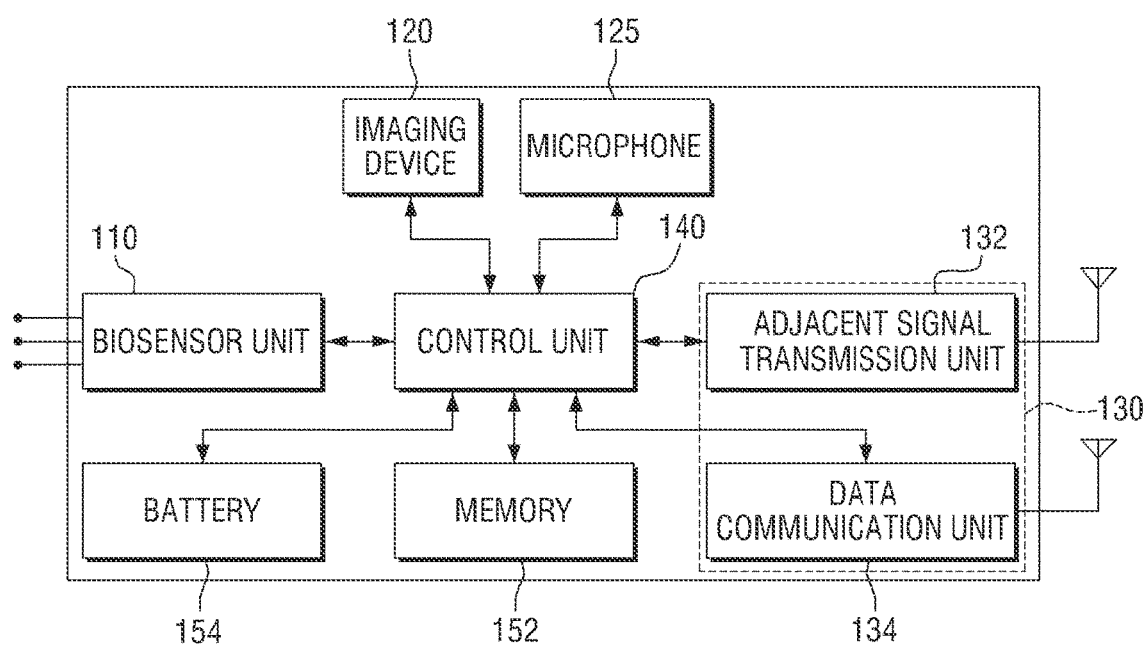
FIG. 3 illustrates a wearable device according to an embodiment of the present disclosure.

FIG. 3 illustrates a wearable device according to an embodiment of the present disclosure.

Referring to FIG. 3, the wearable device includes a biosensor unit 110, an imaging device 120, a microphone 125, an adjacent signal transmitting unit 132, a data communication unit 134, a control unit 140, a memory 152, and a battery 154.

The biosensor unit 110 senses a user's, i.e., a wearer's, biosignals. For example, the biosensor unit 110 includes various sensors for sensing biosignals such as body temperature, respiration volume, heart rate, and blood pressure.

The biosensor unit 110 may measure the user's biorhythms (e.g., at least one of pulse rate, blood pressure, body temperature, and respiration volume) using at least one of a pulse rate sensor, a blood pressure sensor, a temperature sensor, and a respiration volume sensor. The user's respiration volume may also be sensed by a microphone or a pressure sensor.

The biosensor unit 110 may include a plurality of sensors, which are placed at positions appropriate for sensing the various biosignals. For example, the sensors of the biosensor unit 110 may be placed on the user's wrist, on the user's ankle, near the user's heart, near large blood vessels, and around the user's neck.

The imaging device 120, e.g., a camera, a camcorder, etc., captures an external image. Generally, the imaging device 120 may include a photographing unit, a view finder, and a display unit that displays a live view image and a photographed image. The photographing unit may include a lens and an image sensor.

The imaging device 120 may support various photographing modes such as a continuous shooting mode, a shutter speed priority mode, and an aperture priority mode. The imaging device 120 may be controlled and activated by the control unit 140.

An image captured by the imaging device 120 may be stored in the memory 152.

In addition, when a request for a captured image is received, the captured image may be transmitted to an external device via the data communication unit 134.

The microphone 125 senses an external sound, e.g., external sound waves or ultrasonic waves. The microphone 125 may be classified as a dynamic microphone and a condenser microphone, a piezoelectric microphone using a piezoelectric phenomenon, a carbon microphone using contact resistance of carbon particles, a pressure microphone generating an output proportional to sound pressure, and a velocity microphone generating an output proportional to negative particle velocity. The microphone 125 may be controlled by the control unit 140.

An external sound or voice recorded by the microphone 125 may be converted into electrical data and stored in the memory 152.

In addition, when a request for a recorded sound is made, the recorded sound may be transmitted to an external device via the data communication unit 134.

A wireless communication unit 130 includes the adjacent signal transmission unit 132 and the data communication unit 134. The wireless communication unit 130 may be controlled by the control unit 140.

In FIG. 3, each of the adjacent signal transmission unit 132 and the data communication unit 134 include an antenna for communication, but the current embodiment is not limited thereto.

The adjacent signal transmission unit 132 generates an adjacent signal for measuring the distance between the wearable device 100 and the mobile device 200. Basically, the adjacent signal is a wireless signal for distance measurement. The wearable device 100 and the mobile device 200 may be wirelessly linked to each other. As described above, the wearable device 100 and the mobile device 200 may use a local area wireless communication method such as Bluetooth®, WiFi, or infrared communication.

The mobile device 200 receives the adjacent signal from the wearable device 100 and measures the intensity of the adjacent signal. For example, the adjacent signal may include an IDentifier (ID) of the wearable device 100, a distance measurement request command, or a control command for instructing the mobile device 200 to provide information about the current location of the wearable device 100 in order for a user to identify the current location of the wearable device 100.

The data communication unit 134 transmits biosignals measured by the biosensor unit 110 and data including an image captured by the imaging device 120 or a sound recorded by the microphone 125 to the mobile device 200. The data communication unit 134 may use a local area wireless communication method such as an RF signal, an infrared signal, an ultrasonic signal, Bluetooth®, or NFC and a mobile communication method such as 2G/3G/4G or WiBro wireless network service.

Specifically, the data communication unit 134 may periodically transmit biosignals to the mobile device 200. The data communication unit 134 may periodically transmit data including an image or sound to the mobile device 200 according to user settings. The data communication unit 134 may also transmit data including an image or sound at the request of a user. For example, the transmitted data includes a most recently captured image and/or a most recently recorded sound.

The memory 152 may store biosignals, data and/or commands. The memory 152 may include a volatile memory and a nonvolatile memory. For example, the memory 152 may be implemented as at least one of a nonvolatile memory such as a cache, a read only memory (ROM), a programmable ROM (PROM), an erasable programmable ROM (EPROM), an electrically erasable programmable ROM (EEPROM) or a flash memory and a storage medium such as a hard disk drive.

The battery 154 supplies power to all components of the wearable device 100.

The control unit 140 may control all components of the wearable device 100. For example, when receiving a request for biosignals and data including an image or a sound from the mobile device 200, the control unit 140 may activate the biosensor unit 110, the imaging device 120, and/or the microphone 125. Thereafter, the control unit 140 may receive data including an external sound or an image and/or biosignals, and may transmit the received data and/or biosignals to the mobile device 200 via the data communication unit 134.

Figure 4:
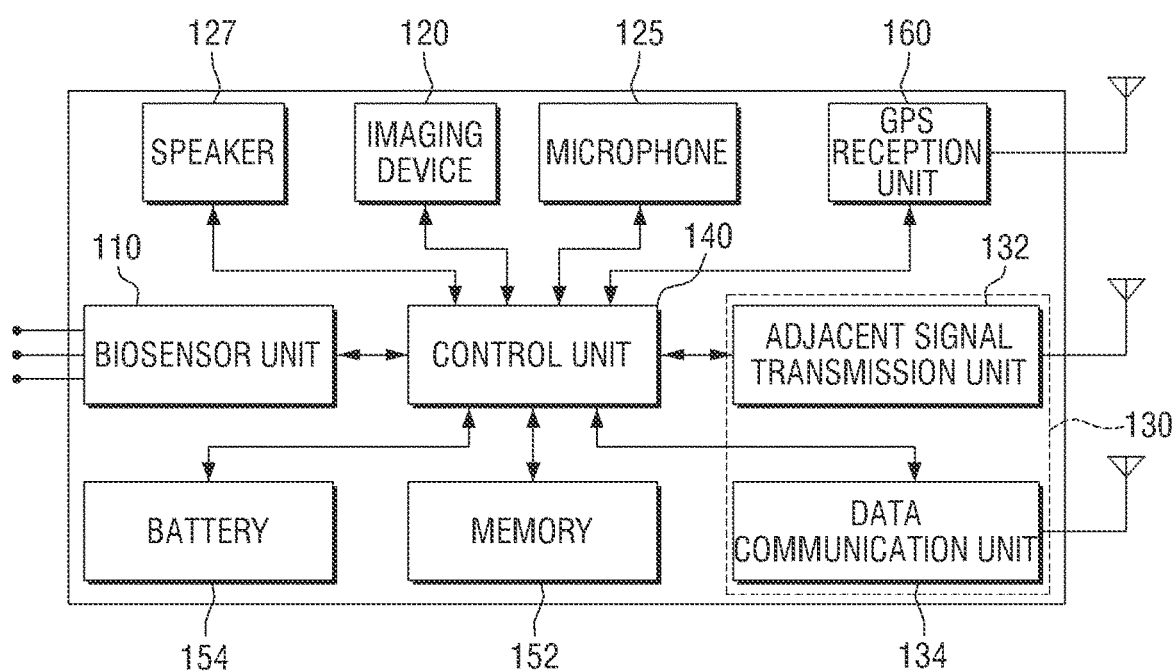
FIG. 4 illustrates a wearable device according to an embodiment of the present disclosure.

FIG. 4 illustrates a wearable device according to an embodiment of the present disclosure. For simplicity, because the biosensor unit 110, the imaging device 120, the microphone 125, the wireless communication unit 130, the adjacent signal transmitting unit 132, the data communication unit 134, the control unit 140, the memory 152, and the battery 154 have already been described above with reference to FIG. 3, these components will not be described in detail again below with reference to FIG. 4.

Referring to FIG. 4, the wearable device operates in substantially the same way as the wearable device described above with reference to FIG. 3, except that the wearable device in FIG. 4 further includes a GPS reception unit 160 and a speaker 127.

The GPS reception unit 160 receives a GPS signal from a GPS satellite in order to obtain GPS location information of the wearable device 102. In addition, the GPS reception unit 160 may receive network position information. The network position information refers to position information measured using A-GPS or base station information of a wireless mobile communication network (such as WiFi, WiBro or 2G/3G/4G). Therefore, the approximate position of the wearable device 102 can be identified from the network position information based on the network.

The GPS position information of the wearable device 102 may first be received. If the GPS position information is not received, information such as the network position information may be received.

The wearable device 102 may receive GPS information of its current location and periodically transmit the GPS information to the mobile device 200. In addition, the wearable device 102 may preferentially transmit biosignals and the GPS information, which are relatively small in size, and additionally request data.

The speaker 127 outputs audio signals. The speaker 127 may be classified as a cone-type speaker using a paper, plastic or metal cone as a diaphragm or a hybrid speaker having a horn placed on the whole surface of a diaphragm to improve efficiency.

When receiving an emergency signal from the mobile device 200, the speaker 127 may output a help request signal. Examples of the help request signal may include a pre-recorded voice, a beep sound, and a siren sound.

For example, when biosignals of a user wearing the wearable device 102 are abnormal, the wearable device 102 may receive an emergency signal from the mobile device 200 or the server 400 through the data communication unit 134. In response to the emergency signal, the speaker 127 output the help request signal.

Figure 5:
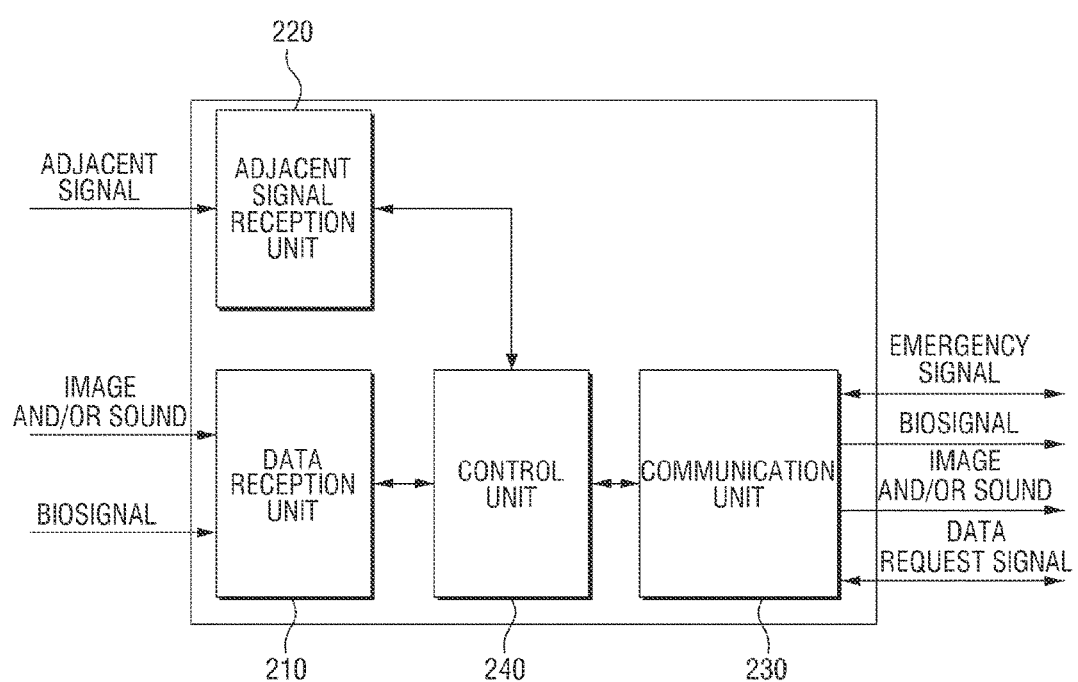
FIG. 5 illustrates a mobile device according to an embodiment of the present disclosure.

FIG. 5 illustrates a mobile device according to an embodiment of the present disclosure.

Referring to FIG. 5, the mobile device includes a data reception unit 210, an adjacent signal reception unit 220, a communication unit 230, and a control unit 240.

The data reception unit 210 may periodically receive biosignals measured by the wearable device 100 and data including an image or a sound. The data reception unit 210 may be wirelessly connected to the wearable device 100. For example, the data reception unit 210 may receive the biosignals or the data using a local area wireless communication method such as an RF signal, an infrared signal, an ultrasonic signal, Bluetooth®, or NFC, or a mobile communication method such as 2G/3G/4G or WiBro wireless network service.

The data reception unit 210 may transmit the received biosignals and/or data to the control unit 240, which may transmit the biosignals and/or data to the server 400 via the communication unit 230. The data reception unit 210 may periodically receive biosignals. At the request of a guardian or a relevant agency, the data reception unit 210 may periodically receive the data in addition to the biosignals.

The adjacent signal reception unit 220 may receive an adjacent signal for measuring a distance between the wearable device 100 and the mobile device. The wearable device 100 and the mobile device may be wirelessly linked to each other. Basically, the adjacent signal is a wireless signal for distance measurement. For example, the wearable device 100 and the mobile device may use a local area wireless communication method such as Bluetooth®, WiFi, or infrared communication.

For example, the adjacent signal reception unit 220 may measure the intensity of the adjacent signal received from the wearable device 100 and determine the distance between the wearable device 100 and the mobile device based the intensity of the received adjacent signal. For example, the adjacent signal may be periodically transmitted from the wearable device 100, and the adjacent signal reception unit 220 may calculate the distance between the wearable device 100 and the mobile device using an average of the intensities of the received adjacent signal.

As another example, the adjacent signal reception unit 220 may calculate the distance between the wearable device 100 and the mobile device by transmitting a signal corresponding to the received adjacent signal.

As another example, the adjacent signal reception unit 220 may calculate the distance between the wearable device 100 and the mobile device using a time required for the adjacent signal to arrive at the mobile device.

The adjacent signal may include an ID of the wearable device 100, a distance measurement request command, and/or a control command for instructing the mobile device to provide information about the current position of the wearable device 100.

The distance between the wearable device 100 and the mobile device may also be calculated by the control unit 240, based on the adjacent signal received by the adjacent signal reception unit 220.

The communication unit 230 is a network interface that connects the mobile device with an external device using a wired or wireless communication method. The communication unit 230 may support a wireless communication method such as Bluetooth, Zigbee, radio frequency identification (RFID), NFC, WLAN, WiBro, 3G mobile communication, or 4G mobile communication, or a wired communication method such as wired LAN, RS232 communication or wired public switched telephone network (PSTN) communication. The communication unit 230 may be controlled by the control unit 240.

For example, the communication unit 230 may transmit biosignals and data including an image or a sound to the server 400. The communication unit 230 may receive an emergency signal from the server 400 and transmit the emergency signal to the wearable device 100. The communication unit 230 may also receive a data request signal from the second mobile device 300 (e.g., a mobile device of a guardian or a system of a relevant agency). The operation of the communication unit 230 may be controlled by the control unit 240.

The control unit 240 may control all components of the mobile device 200.

For example, when an intensity of an adjacent signal is less than or equal to a preset value or when the control unit 240 receives an emergency signal from the server 400, the control unit 240 may request the wearable device 100 to provide biosignals and data and then may transmit the received biosignals and data to the server 400.

The control unit 240 may calculate the distance between the wearable device 100 and the mobile device 200 using an adjacent signal received through the adjacent signal reception unit 220. As described above, the distance between the wearable device 100 and the mobile device may be calculated by measuring the intensity of the adjacent signal, calculating a response time of the adjacent signal, or using the average of the adjacent signals.

If the intensity of the adjacent signal is less than or equal to the preset value, that is, if the distance between the wearable device 100 and the mobile device is greater than or equal to a predetermined distance, the control unit 240 may determine that an emergency situation has occurred. In this case, the control unit 240 may transmit an emergency signal requesting GPS information and an image and/or a sound about a current situation, to the wearable device 100, through the communication unit 230.

When receiving the GPS information and the image and/or sound from the wearable device 100, the control unit 240 may transmit the received data to the server 400. Here, the control unit 240 may preferentially request biosignals or GPS information, and additionally request data including an image and/or a sound.

When the communication unit 230 receives a data request signal from the second mobile device 300 (e.g., a mobile phone of a guardian or a relevant agency), the control unit 240 may transmit an emergency signal to the wearable device 100. The mobile device may receive GPS information and data including an image or sound about the current situation from the wearable device 100 and transmit the received GPS information and data to the second mobile device 300.

Examples of the mobile device illustrated in FIG. 5 include a computer, an ultra mobile PC (UMPC), a work station, a net-book computer, a PDA, a portable computer, a wireless phone, a web tablet, a wireless phone, a mobile phone, a smartphone, a portable multimedia player (PMP), a portable game console, a digital camera, a digital audio recorder, a digital audio player, a digital picture recorder, a digital picture player, a digital video recorder, a digital video player, a device capable of transmitting and receiving information in a wireless environment, one of various electronic devices constituting a home network, one of various electronic devices constituting a computer network, one of various electronic devices constituting a telematics network, or one of various components of a computing system.

Figure 6:
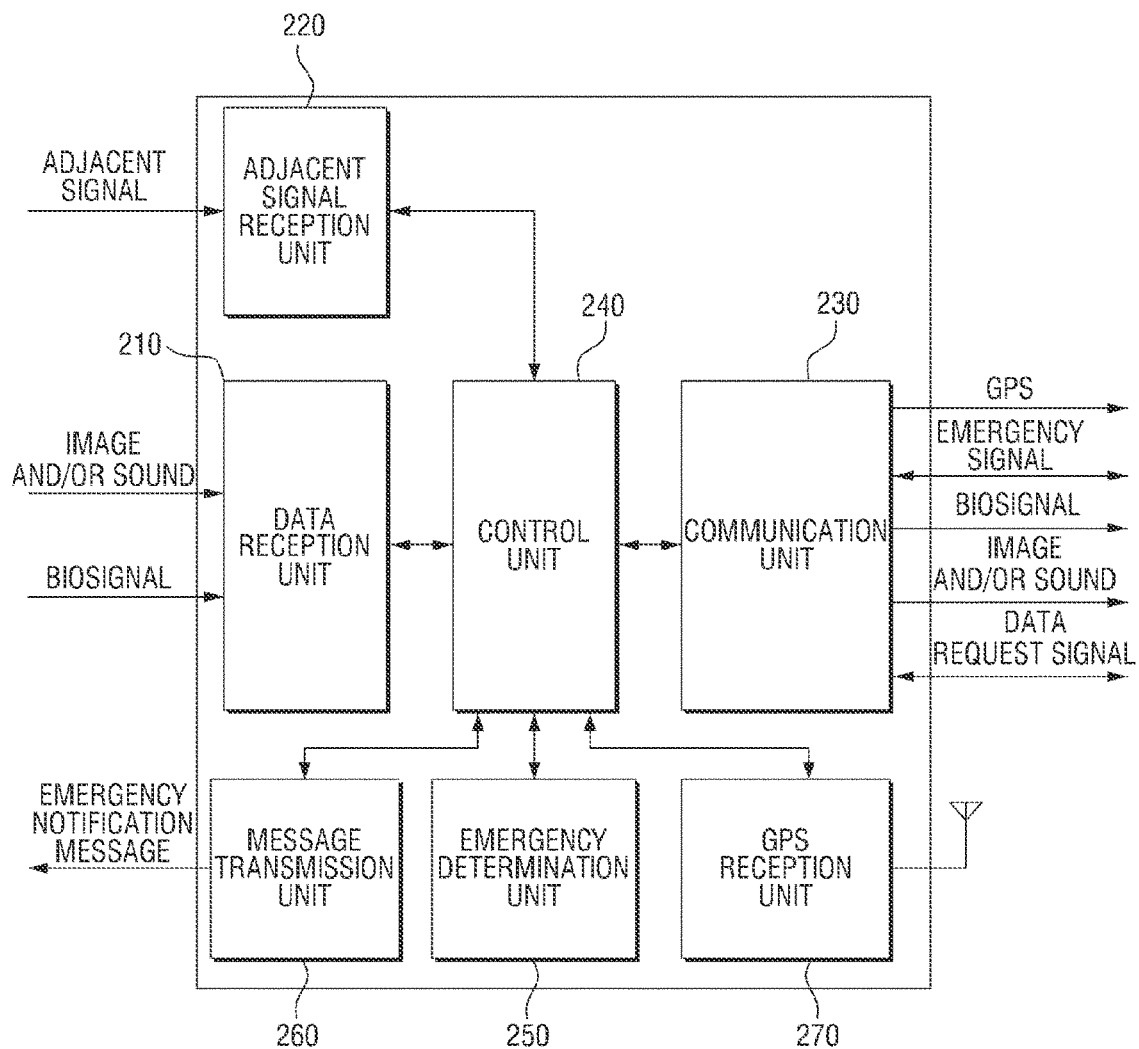
FIG. 6 illustrates a mobile device according to an embodiment of the present disclosure.

FIG. 6 illustrates a mobile device according to an embodiment of the present disclosure. For simplicity, because the data reception unit 210, the adjacent signal reception unit 220, the communication unit 230, and the control unit 240 have already been described above with reference to FIG. 5, these components will not be described in detail again below with reference to FIG. 6.

Referring to FIG. 6, the mobile device operates in substantially the same way as the mobile device described above with reference to FIG. 5, except that the mobile device in FIG. 6 further includes an emergency situation determination unit 250, a message transmission unit 260, and a GPS reception unit 270.

The emergency situation determination unit 250 may determine whether a user's heath condition is abnormal by analyzing biosignals measured by the wearable device 100. That is, the emergency situation determination unit 250 may receive and store the biosignals and determine whether an emergency situation has occurred by analyzing the stored biosignals. The biosignals may include the user's body temperature, respiration volume, heart rate, and blood pressure.

The emergency situation determination unit 250 may store data (biosignals) in a normal state and determine whether an emergency situation has occurred by comparing the received biosignals with the biosignals in the normal state. When the emergency situation determination unit 250 determines that an emergency situation has occurred, the control unit 240 transmits an emergency signal to the wearable device 100. The control unit 240 may also transmit the emergency signal to the server 400, the mobile device 300 of a guardian, and a relevant agency.

When the emergency situation determination unit 250 determines that an emergency situation has occurred, the message transmission unit 260 may transmit an emergency notification message to the server 400, the mobile device 300 of the guardian, and the relevant agency. The emergency notification message may include data including an image and/or a sound captured by the wearable device 100, GPS information received by the wearable device 100, or biometric information measured by the wearable device 100. The message transmission unit 260 may transmit the emergency notification message by using short message service (SMS) or multimedia messaging service (MMS), by providing a URL of a related link, or by placing a voice call.

The GPS reception unit 270 receives a GPS signal from a GPS satellite in order to obtain GPS location information of the wearable device 100.

In addition, the GPS reception unit 270 may receive network position information, i.e., position information measured using A-GPS or base station information of a wireless mobile communication network (such as WiFi, WiBro, or 2G/3G/4G). Therefore, the approximate position of the wearable device 100 can be identified from the network position information based on the network. The GPS position information of the wearable device 100 may first be received.

If the GPS position information is not received, information such as the network position information may be received.

When receiving an emergency signal from the server 400, the control unit 240 may transmit GPS information received by the GPS reception unit 270 or GPS information received by the wearable device 100 to the server 400. When receiving a data request signal from the guardian or the relevant agency, the control unit 240 may transmit the GPS information received by the GPS reception unit 270 or the GPS information received by the wearable device 100 to the guardian or the relevant agency.

Figure 7:
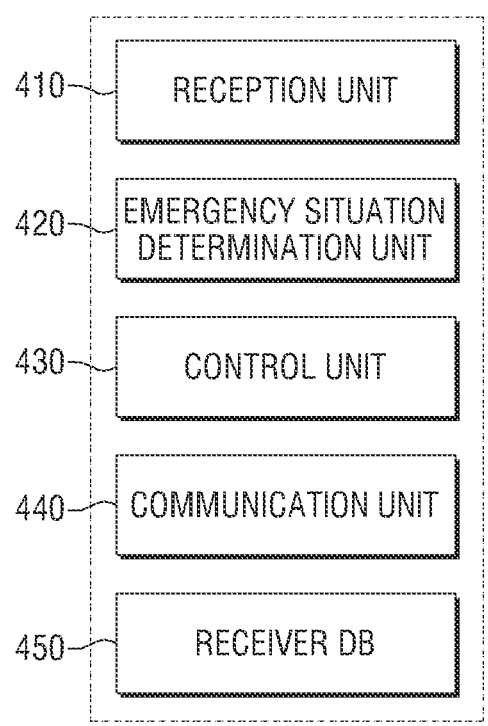
FIG. 7 illustrates an emergency notification server according to an embodiment of the present disclosure.

FIG. 7 illustrates an emergency notification server according to an embodiment of the present disclosure.

Referring to FIG. 7, the emergency notification server includes a reception unit 410, an emergency situation determination unit 420, a control unit 430, a communication unit 440, and a receiver database (DB) 450.

The reception unit 410 may receive biosignals from the mobile device 200. Further, the reception unit 410 may periodically receive an intensity of an adjacent signal between the wearable device 100 and the mobile device 200. The reception unit 410 may also receive data including an image and/or a sound from the mobile device 200.

The reception unit 410 may further receive a GPS signal from the mobile device 200 or the wearable device 100.

When the intensity of an adjacent signal is less than or equal to a preset value or when the emergency situation determination unit 420 determines that an emergency situation has occurred, the control unit 430 may transmit the GPS signal to a receiver group (e.g., a group including the second mobile device 300) stored in the receiver DB 450.

The emergency situation determination unit 420 may receive and store the biosignals and determine whether an emergency situation has occurred by analyzing the stored biosignals. For example, the emergency situation determination unit 420 may store data (biosignals) in a normal state and later determine whether an emergency situation has occurred by comparing the received biosignals with the biosignals in the normal state.

When the emergency situation determination unit 420 identifies an emergency situation occurrence, the control unit 430 transmits an emergency signal to the mobile device 200. The control unit 430 may also transmit the emergency signal to the receiver group (e.g., a group including the second mobile device 300) stored in the receiver DB 450.

When the intensity of the adjacent signal is less than or equal to the preset value or when the emergency situation determination unit 420 identifies an emergency situation occurrence, the control unit 430 may generate an emergency signal and request the mobile device 200 to provide data including the most recently received sound and image.

The communication unit 440 may transmit the emergency signal to the mobile device 200 or the receiver group (e.g., a group including the second mobile device 300) stored in the receiver DB 450 and may transmit data including an image and/or a sound to the mobile device 200 or the receiver group.

When requested by the second mobile device 300, the communication unit 440 may provide data including an image and/or a sound, biosignals, and a GPS signal to the second mobile device 300. For example, the data transmitted to the second mobile device 300 may be data most recently received by the server 400.

The receiver DB 450 may store information about the receiver group. The receiver DB 450 may be configured as a storage device and include a memory (e.g. a volatile memory and a nonvolatile memory). For example, the memory may be implemented as at least one of a nonvolatile memory such as a cache, a ROM, a PROM, an EPROM, an EEPROM, or a flash memory, and a storage medium such as a hard disk drive.

When the emergency situation determination unit 420 identifies an emergency situation occurrence, the receiver DB 450 may transmit information about a user included in the receiver group to the control unit 430 or the communication unit 440.

Figure 8:
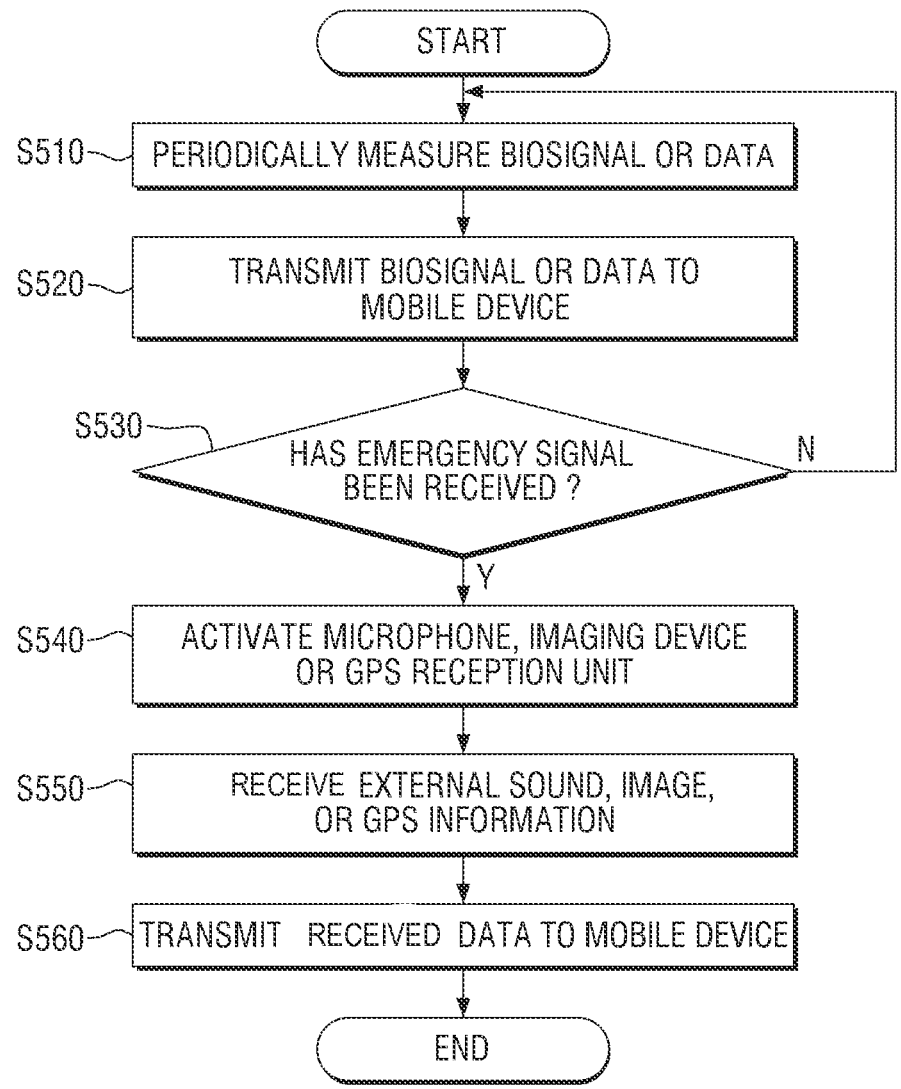
FIG. 8 is a flowchart illustrating an operation of a wearable device according to an embodiment of the present disclosure.

FIG. 8 is a flowchart illustrating an operation of a wearable device according to an embodiment of the present disclosure.

Referring to FIG. 8, in step S510, the wearable device periodically measures biosignals using the biosensor unit 110 and/or captures data including an external image or a sound using the imaging device 120, or the microphone 125.

In step S520, the wearable device periodically transmits the measured biosignals and/or captured data to a mobile device.

In step S530, the wearable device determines whether an emergency signal has been received. The emergency signal may be generated by the mobile device or a server.

If the emergency signal has been received, in step S540, the wearable device activates a microphone, an imaging device, and/or a GPS reception unit 160 therein.

In step S550, an external sound, an image, and/or GPS information are received in the wearable device using the activated microphone, the activated imaging device, and/or the activated GPS reception unit.

In step S560, the received data is transmitted to the mobile device.

However, if the emergency signal has not been received in step S530, the operation returns to step S510.

Figure 9:
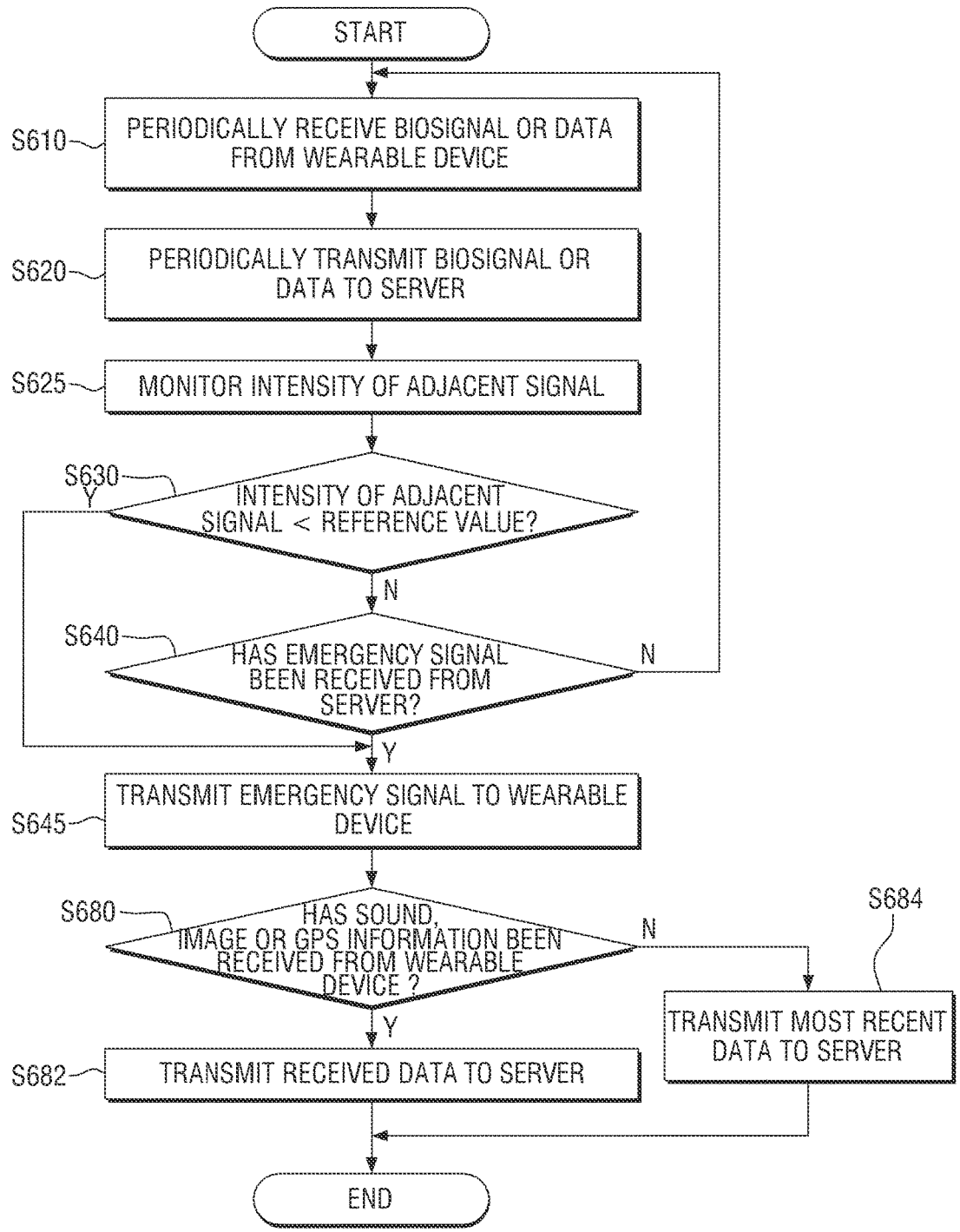
FIG. 9 is a flowchart illustrating an operation of a mobile device according to an embodiment of the present disclosure.

FIG. 9 is a flowchart illustrating an operation of a mobile device according to an embodiment of the present disclosure.

Referring to FIG. 9, in step S610, the mobile device periodically receives biosignals and/or data including an external image and/or a sound from a wearable device.

In step 620, the mobile device periodically transmits the received biosignals and/or data to a server.

In step S625, the mobile device receives an adjacent signal and monitors the intensity of the adjacent signal.

In step S630, the mobile device determines whether the intensity of the adjacent signal is less than a predetermined reference value.

If the intensity of the adjacent signal is less than the predetermined reference value, the mobile device determines that an emergency situation has occurred and transmits an emergency signal to the wearable device in step S645. At the same time, the mobile device may transmit the emergency signal to a server or a mobile device of a guardian.

However, if the intensity of the adjacent signal is not less than the predetermined reference value in step S630, the mobile device determines whether an emergency signal has been received from a server in step S640.

When the emergency signal is received from the server in step S640, the mobile device determines that an emergency situation has occurred and transmits the emergency signal to the wearable device in step S645.

In step S680, the mobile device determines whether a sound, an image, and/or GPS information has been received from the wearable device, in response to the emergency signal.

If the sound, the image, and/or the GPS information have been received from the wearable device, the mobile device transmits the received data to the server in step S682.

However, if the sound, the image, and/or the GPS information have not been received from the wearable device in step S680, the mobile device transmits the most recently received data to the server in step S684.

In addition, when the emergency signal is not received from the server in step S640, the operation returns to step S610.

Figure 10:
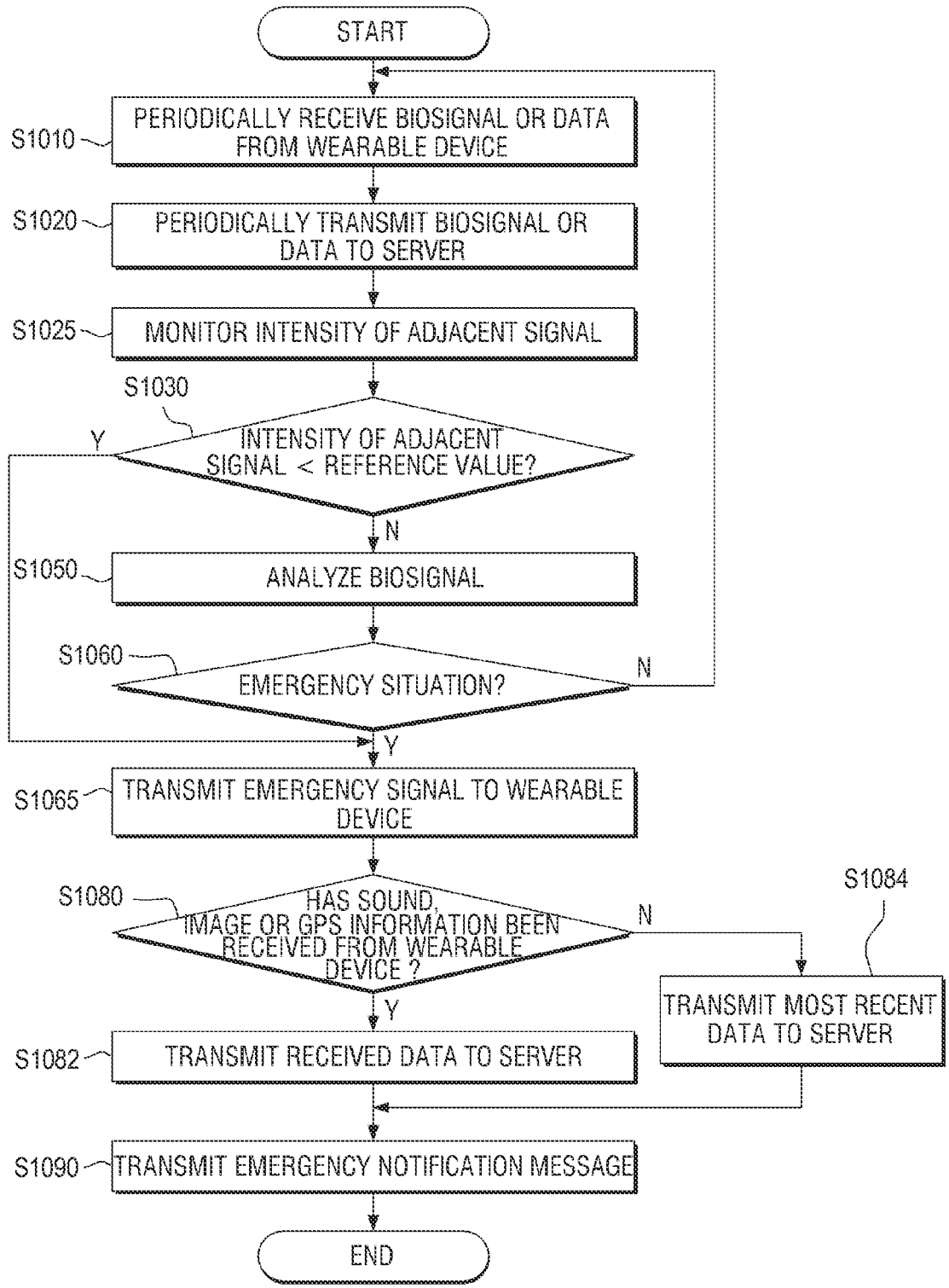
FIG. 10 is a flowchart illustrating an operation of a mobile device according to an embodiment of the present disclosure.

FIG. 10 is a flowchart illustrating an operation of a mobile device according to an embodiment of the present disclosure.

Referring to FIG. 10, in step S1010, the mobile device periodically receives biosignals and/or data including an external image and/or a sound from a wearable device.

In step S1020, the mobile device periodically transmits the received biosignals and/or data to a server.

In step S1025, the mobile device receives an adjacent signal, and monitors the intensity of the adjacent signal.

In step S1030, the mobile device determines whether the intensity of the adjacent signal is smaller than a predetermined reference value.

If the intensity of the adjacent signal is smaller than the predetermined reference value, the mobile device determines that an emergency situation has occurred and transmits an emergency signal to the wearable device in step S1065. At the same time, the mobile device may transmit the emergency signal to the server or a mobile device of a guardian.

However, if the intensity of the adjacent signal is not smaller than the predetermined reference value in step S1030, the mobile device analyzes the biosignals received from the wearable device in step S1050.

In step S1060, the mobile device determines whether the analysis result of the biosignals indicates an emergency situation.

When the analysis result of the biosignals indicates the emergency situation, the mobile device transmits an emergency signal to the wearable device in step S1065.

In step S1080, the mobile device determines whether a sound, an image, and/or GPS information has been received from the wearable device, in response to the emergency signal.

If the sound, the image, and/or the GPS information have been received from the wearable device in step S1080, the mobile device transmits the received data to the server in step S1082).

However, if the sound, the image, and/or the GPS information have not been received from the wearable device in step S1080, the mobile device transmits the most recently received data to the server in step S1084).

In step S1090, the mobile device transmits the emergency notification message to the wearable device, the server, a mobile device of a guardian, etc.

In addition, when the analysis result of the biosignals does not indicate the emergency situation in step S1060, the operation returns to step S1010

Figure 11:
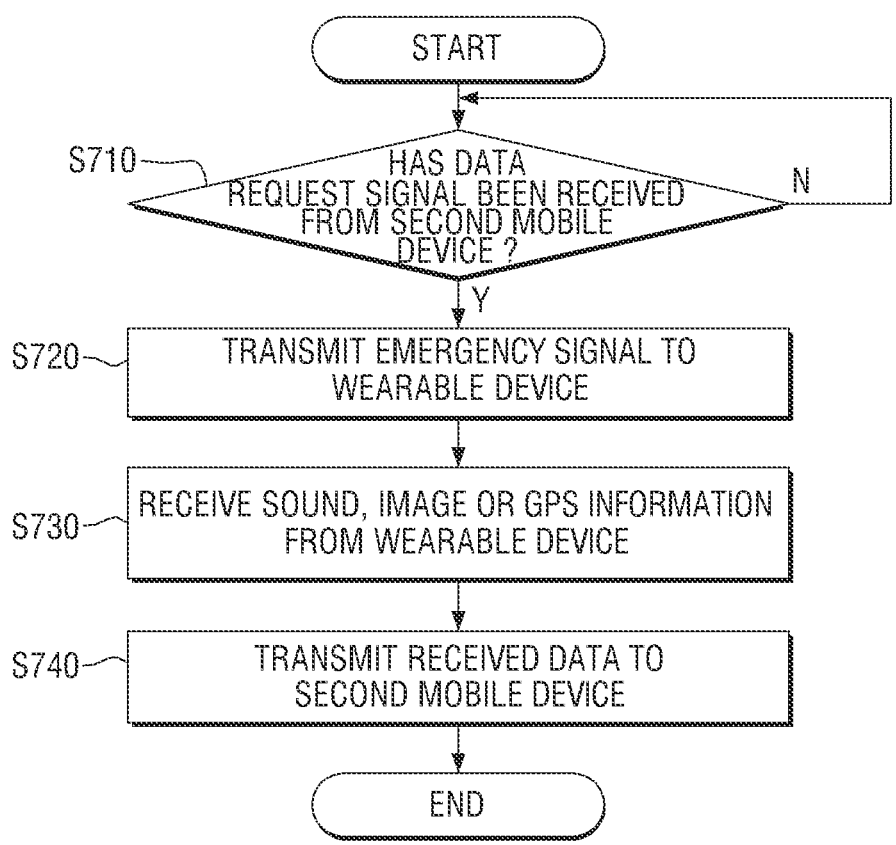
FIG. 11 is a flowchart illustrating an operation of a mobile device according to an embodiment of the present disclosure.

FIG. 11 is a flowchart illustrating an operation of a mobile device according to an embodiment of the present disclosure.

Referring to FIG. 11, in step S710, the mobile device determines whether a data request signal has been received from a second mobile device. Examples of the second mobile device may include the mobile device 300 of a guardian and a relevant agency system, as illustrated in FIG. 2.

If the data request signal has been received in step S710, the mobile device transmits an emergency signal to a wearable device in step S720.

In step S730, a sound, an image, and/or GPS information is received from the wearable device.

In step S740, the mobile device transmits the received data to the second mobile device.

Figure 12:
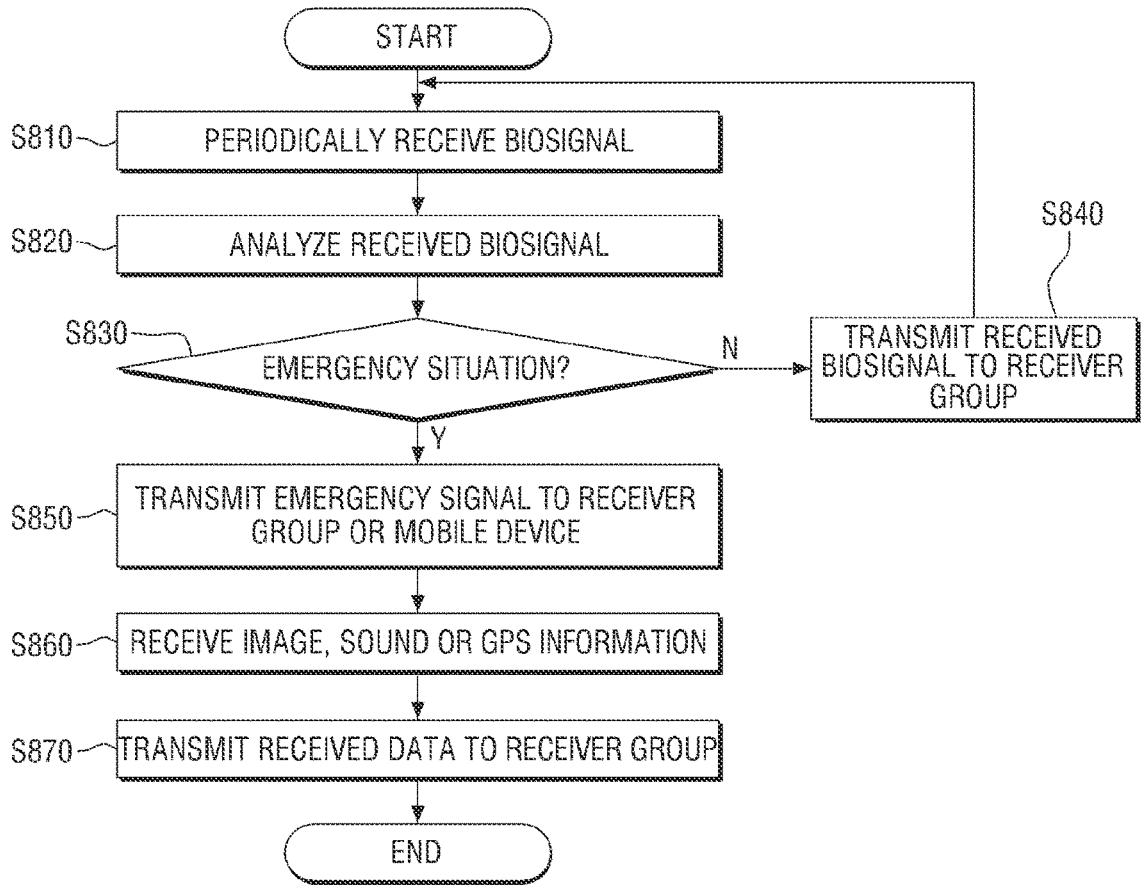
FIG. 12 is a flowchart illustrating an operation of an emergency notification server according to an embodiment of the present disclosure.

FIG. 12 is a flowchart illustrating an operation of an emergency notification server according to an embodiment of the present disclosure.

Referring to FIG. 12, in step S810, the emergency notification server periodically receives biosignals from a mobile device.

In step S820, the emergency notification server analyzes the received biosignals in order to determine whether an emergency situation has occurred.

In step S830, the emergency notification server determines whether an emergency situation has occurred, based on the analyzed biosignals.

When it is determined that the emergency situation has occurred, the emergency notification server transmits an emergency signal to a receiver group or the mobile device in step S850. As described above, information about the receiver group may be stored in a receiver DB. The receiver group may include a mobile device of a guardian and a system of a relevant agency.

In step S860, a sound, an image, and/or GPS information is received from the mobile device. As described above, when receiving the emergency signal, the mobile device transmits the emergency signal to the wearable device, which activates a microphone, an imaging device, and/or a GPS reception unit and receives an external sound, an image, and/or GPS information using the microphone, the imaging device, and/or the GPS reception unit, respectively.

The received sound, image, and/or GPS information is transmitted from the wearable device to the mobile device, which transmits the received sound, image, and/or GPS information to the server.

In step S870, the server transmits data including the received sound, the image, and/or GPS information to the receiver group.

However, when it is determined that the emergency situation has not occurred in step S830, the emergency notification server transmits the received biosignals to the receiver group in step S840. Thereafter, the operation returns to step S810.

As described above, the emergency notification system periodically transmits health information of the user wearing the wearable device to a server via a mobile device, so that the server can analyze the health information. If the result of analysis indicates an emergency situation, the server may immediately notify a guardian or a relevant agency of the emergency situation.

In the emergency situation, the server may provide an external image or a sound received using the wearable device and GPS information to assist the guardian and/or the relevant agency in rapidly dealing with the emergency situation. At normal times, i.e., non-emergency situations, the emergency notification system may check the health condition of the user by monitoring the biometric information of the user.

Figure 13:
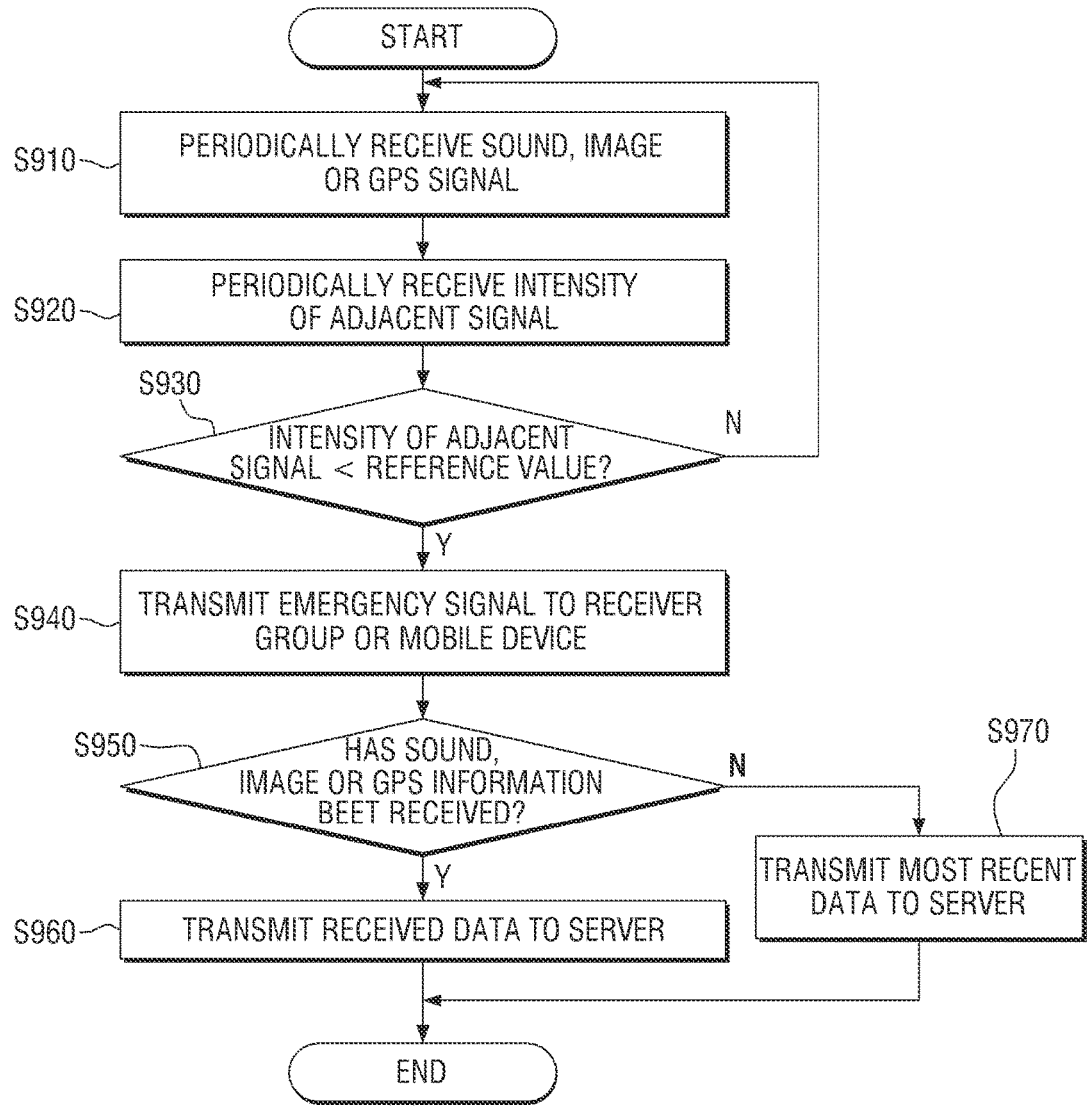
FIG. 13 is a flowchart illustrating an operation of an emergency notification server according to an embodiment of the present disclosure.

FIG. 13 is a flowchart illustrating an operation of an emergency notification server according to an embodiment of the present disclosure.

Referring to FIG. 13, in step S910, the emergency notification server periodically receives data including a sound, an image, and/or a GPS signal from a mobile device. The data captured by a wearable device and transmitted to the mobile device.

In step S920, the emergency notification server periodically receives an intensity of an adjacent signal. As described above, the emergency notification server may measure the distance between the wearable device and the mobile device using the intensity of the adjacent signal. The adjacent signal may be periodically transmitted from the wearable device.

In step S820, the emergency notification server analyzes the received biosignals to determine whether an emergency situation has occurred by analyzing the stored biosignals.

In step S930, the emergency notification server determines whether the intensity of the adjacent signal is less than a preset reference value.

If the intensity of the adjacent signal is less than the predetermined reference value, the emergency notification server determines that an emergency situation has occurred and transmits an emergency signal to a receiver group or the mobile device in step S940. Accordingly, the emergency notification server may request the wearable device to provide information about the current situation and notify a guardian or a relevant agency of the emergency situation.

In step S950, the emergency notification server determines whether a sound, an image, and/or GPS information has been received from the mobile device in response to the emergency signal.

If the sound, the image, and/or the GPS information have been received from the mobile device, the emergency notification server transmits the received data to the receiver group in step S960.

However, if the sound, the image, and/or the GPS information have not been received from the mobile device in step S950, the emergency notification server transmits data most recently received from the mobile device to the receiver group in step S970.

However, if the intensity of the adjacent signal is not less than the predetermined reference value, the operation returns to step S910.

As described above, the emergency notification system may measure a wireless signal intensity between the wearable device and the mobile device. The wireless signal intensity may be measured using an adjacent signal, and the adjacent signal may have a different type and frequency from a channel that transmits data.

When the measured intensity of the adjacent signal is less than or equal to a predetermined reference value, it is determined that an emergency situation has occurred. For example, there may be a situation where the wearable device is separated from a user's body in an accident.

When it is determined that an emergency situation has occurred, based on the intensity of the adjacent signal, the emergency notification server may immediately notify a guardian or a relevant agency of the emergency situation. In the emergency situation, the emergency notification server may provide an external image or a sound captured using the wearable device and GPS information. However, if a signal between the wearable device and the mobile device is weak, data may not be normally transmitted. In this case, the emergency notification server may transmit an image or a sound, and GPS information most recently received from the mobile device to the receiver group. Accordingly, the receiver group can rapidly deal with the emergency situation by collecting information about the emergency situation.

While the present disclosure has been particularly shown and described with reference to certain embodiments thereof, it will be understood by those of ordinary skill in the art that various changes in form and details may be made therein without departing from the spirit and scope of the present disclosure as defined by the following claims and their equivalents.

What is claimed is:

1. An emergency notification system comprising:
a wearable device that senses biosignals of a user wearing the wearable device and captures environment data; and
a mobile device, which is wirelessly connected to the wearable device, that periodically receives at least one of the biosignals and the environment data from the wearable device, determines a distance between the mobile device and the wearable device based on an intensity of an adjacent signal received from the wearable device, periodically transmits the at least one of the biosignals and the environment data to a server, requests the wearable device to provide the at least one of the biosignals and the environment data, and transmits global positioning system (GPS) information and the received at least one of the biosignals and the environment data to the server when the intensity of the adjacent signal is less than or equal to a preset value or when an emergency signal is received from the server,
wherein the environment data comprises at least one of an image and a sound.

2. The system of claim 1, wherein the wearable device comprises:
a biosensor unit that senses the biosignals of the user;
an adjacent signal transmission unit that generates the adjacent signal;

a data communication unit that wirelessly transmits the biosignals and the environment data to the mobile device; and a control unit that activates the biosensor unit, when a request for the biosignals is received from the mobile device.

3. The system of claim 2, wherein the wearable device further comprises a GPS reception unit that receives a GPS signal from a satellite.

4. The system of claim 3, wherein the wearable device generates GPS information of a current position, based on the received GPS signal, and periodically transmits the GPS information to the mobile device.

5. The system of claim 2, wherein the wearable device further comprises a speaker that outputs a help request signal, when the emergency signal is received from the mobile device.

6. The system of claim 2, wherein the biosensor unit measures at least one of an electrocardiogram, blood pressure, body temperature, and respiration volume.

7. The system of claim 1, wherein the wearable device periodically transmits the at least one of the biosignals and the data to the mobile device.

8. The system of claim 1, wherein the wearable device comprises at least one of an imaging device that captures the image, and a microphone that senses the sound.

9. The system of claim 1, wherein the mobile device receives the biosignals and determines whether an emergency situation has occurred, based on the received biosignals.

10. The system of claim 9, wherein the mobile device transmits an emergency notification message to a second mobile device, when the emergency situation has occurred.

11. The system of claim 1, wherein the mobile device provides the at least one of the biosignals and the environment data to a second mobile device.

12. An emergency notification server comprising:

a transceiver that periodically receives, from a first mobile device, biosignals and an intensity of an adjacent signal between the first mobile device and a wearable device that senses the biosignals; and a controller that determines whether an emergency situation has occurred based on the received biosignals, generates an emergency signal requesting the first mobile device to provide data comprising a most recently received sound, an image, and global positioning system (GPS) information when the intensity of the adjacent signal is less than or equal to a preset value or when the emergency situation has occurred, and controls the transceiver to transmit the emergency signal to the first mobile device or to transmit the emergency signal and the data to a second mobile device.

13. The server of claim 12, further comprising a receiver database (DB) that stores information about a receiver group for receiving the emergency signal.

14. A mobile device that is wirelessly connected to a wearable device, the mobile device comprising:

a transceiver that periodically receives, from the wearable device, at least one of biosignals sensed by the wearable device and environment data captured by the wearable device, and that periodically transmits the received at least one of the biosignals and the environment data to a server; and a controller that requests the wearable device to provide the at least one of the biosignals and the environment data, determines whether an emergency situation has occurred, based on the received at least one of the biosignals and the environment data, transmits global positioning system (GPS) information to a server when an intensity of an adjacent signal received from the wearable device is less than or equal to a preset value or when an emergency signal is received from the server, and controls the transceiver to transmit an emergency signal to the wearable device, when the emergency situation has occurred, wherein the environment data comprises at least one of an image and a sound of a current environment of the wearable device.

15. The mobile device of claim 14, further comprising an adjacent signal reception unit that determines a distance between the mobile device and the wearable device based on an intensity of the adjacent signal generated by the wearable device.

16. The mobile device of claim 15, wherein the controller controls the transceiver to transmit the received at least one of the biosignals and the environment data to the server, when the intensity of the adjacent signal is less than or equal to a preset value or when the emergency signal is received from the server.

17. The mobile device of claim 14, wherein the controller controls the transceiver to transmit an emergency notification to a receiver group, when the emergency situation has occurred.

18. The mobile device of claim 17, wherein the receiver group comprises at least one of a guardian of a user wearing the wearable device and an emergency agency.

* * * * *